United States Patent
Tanassi et al.

(10) Patent No.: US 10,034,606 B2
(45) Date of Patent: Jul. 31, 2018

(54) OPTICAL EQUIPMENT FOR OBSERVATION OF THE IRIDOCORNEAL ZONE, METHODS OF MEASURING AND/OR EVALUATING THE IRIDOCORNEAL ZONE

(71) Applicant: NIDEK CO., LTD., Gamagori-shi, Aichi (JP)

(72) Inventors: Cesare Tanassi, Milan (IT); Phil Buscemi, Milan (IT); Federico Carraro, Milan (IT); Andrea De Giusti, Milan (IT); Mattia Minozzi, Milan (IT); Simone Pajaro, Milan (IT); Michele Pascolini, Milan (IT); Nicola Codogno, Milan (IT)

(73) Assignee: NIDEK CO., LTD., Gamagori-shi (JP)

( * ) Notice: Subject to any disclaimer, the term of this patent is extended or adjusted under 35 U.S.C. 154(b) by 0 days.

(21) Appl. No.: 15/314,463

(22) PCT Filed: Apr. 30, 2015

(86) PCT No.: PCT/EP2015/059458
§ 371 (c)(1),
(2) Date: Nov. 28, 2016

(87) PCT Pub. No.: WO2015/180923
PCT Pub. Date: Dec. 3, 2015

(65) Prior Publication Data
US 2017/0231491 A1 Aug. 17, 2017

(30) Foreign Application Priority Data
May 30, 2014 (IT) .............................. CO2014A0018

(51) Int. Cl.
*A61B 3/14* (2006.01)
*A61B 3/00* (2006.01)
*A61B 3/117* (2006.01)

(52) U.S. Cl.
CPC ............ *A61B 3/117* (2013.01); *A61B 3/0025* (2013.01); *A61B 3/0091* (2013.01); *A61B 3/14* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS 6,354,705 B1  3/2002  Hirohara et al.
2011/0282331 A1* 11/2011 Brennan ................ A61B 3/102
606/4

(Continued)

FOREIGN PATENT DOCUMENTS

CN  1 044 214 A   8/1990
EP  1 464 271 A1  10/2004
(Continued)

OTHER PUBLICATIONS

Aug. 4, 2015 International Search Report issued in International Patent Application No. PCT/EP2015/059458.

*Primary Examiner* — Mohammed Hasan
(74) *Attorney, Agent, or Firm* — Oliff PLC (57) ABSTRACT

An optical equipment suitable for observation of an iridocorneal annular zone of an eye including: an illumination assembly, including at least one illumination electric device for illuminating the zone with a plurality of illumination optical paths for illumination light beams going to a corresponding plurality of sub-portions, an image capturing assembly, including at least one image capturing electric device for capturing images of the zone with a plurality of imaging optical paths for imaging light beams coming from a corresponding plurality of sub-portions, and a front optical assembly having a front surface located close to front surface of an eye, a rear surface located far from front
(Continued)

surface of an eye, and including a central portion between the front and rear surfaces and a lateral portion around the central portion; the front optical assembly is stationary; all imaging optical paths pass through central portion between the front and rear surfaces.

20 Claims, 9 Drawing Sheets

(58) Field of Classification Search
USPC .................................................. 351/200–246
See application file for complete search history.

(56) References Cited

U.S. PATENT DOCUMENTS

2014/0354951 A1\* 12/2014 Izatt ...................... A61B 3/102
351/206
2017/0290508 A1\* 10/2017 Vadakke Matham .. A61B 3/117

FOREIGN PATENT DOCUMENTS

| JP | S57-153632 A | 9/1982 |
| JP | H03-45235 A | 2/1991 |
| WO | 2013/188885 A1 | 12/2013 |

\* cited by examiner

OPTICAL EQUIPMENT FOR OBSERVATION OF THE IRIDOCORNEAL ZONE, METHODS OF MEASURING AND/OR EVALUATING THE IRIDOCORNEAL ZONE

TECHNICAL FIELD

The present invention relates to "gonioscopy", more in particular to an optical equipment suitable for observation of at least a portion of an iridocorneal annular zone of an eye and to measuring and/or evaluating methods enabled by such equipment.

BACKGROUND ART

Gonioscopy is an eye examination that is very useful and effective in monitoring and diagnosing various eye conditions associated in particular to glaucoma; it is used by ophthalmologists and optometrists as a primary examination for glaucomatous patients; typically, it is carried out through the use of an indirect gonioscopic lens.

The instruments that are commercially available at present have some drawbacks. They allow only human interpretation. They allow to observe only few and/or limited portions of an iridocorneal zone of an eye; therefore, if an ophthalmologist wants to observe the entire iridocorneal site, he must apply and remove the instrument, in direct contact with the patient eye. Moreover, this contact procedure implies several risks, including corneal scratches, and requires a skilled operator to be carried out; the entire process also requires a careful sterilization of the instrument and to anaesthetize the patient eye.

SUMMARY

It is the general task of the present invention to improve gonioscopy.

If improved, gonioscopy will be used more by more ophthalmologists and optometrists and by other persons with less skills and therefore, for example, a better and faster diagnosis of glaucoma will be possible.

The basic idea behind the present invention is to use a plurality of illumination optical paths for one or more illumination light beams for illuminating an iridocorneal annular zone of an eye and to capture a plurality of images of the zone from a corresponding plurality of imaging optical paths for one or more imaging light beams without moving the lens applied to the eye.

The images may be captured contemporaneously or at different times, i.e. sequentially one immediately after the other in a short time.

The present invention is defined by the appended claims that have to be considered an integral part of the present description.

The first and main aspect the present invention corresponds to an optical equipment suitable for observation of at least a portion of an iridocorneal annular zone of an eye comprising: an illumination assembly, comprising at least one illumination electric device, for illuminating at least a portion of an iridocorneal annular zone of an eye, and having a plurality of illumination optical paths for one or more illumination light beams going to a corresponding plurality of sub-portions of said portion, an image capturing assembly, comprising at least one image capturing electric device, for capturing images of at least a portion of an iridocorneal annular zone of an eye, and having a plurality of imaging optical paths for one or more imaging light beams coming from a corresponding plurality of sub-portions of said portion, and a front optical assembly having a front surface designed to be located close to the front surface of an eye, a rear surface designed to be located far from the front surface of an eye, and comprising a central portion located between the front surface and the rear surface and a lateral portion located around the central portion; the front optical assembly is stationary; all the imaging optical paths pass through the central portion between the front surface and the rear surface; the lateral portion comprises a reflecting element surrounding the central portion and designed to provide a reflection along all the imaging optical paths. Therefore, when this solution is used, at least the image capturing assembly is far from the observed eye.

According to the present invention, natural light that is rather diffused (i.e. coming from different directions) and rather weak does not allow the desired observation of the iridocorneal annular zone of an eye; all gonioscopic lenses, including the one disclosed in document EP1464271A1, use natural light.

According to the present invention, the (artificial) light beams illuminating the iridocorneal zone of the eye enter the eye at a high inclination with respect to the eye axis, preferably higher than 45°; this is totally different from the teaching of U.S. Pat. No. 6,354,705B1.

A second aspect of the present invention corresponds to a method of determining an amplitude of an iridocorneal angle at at least one position of an iridocorneal zone of an eye, comprising the steps of: illuminating the iridocorneal zone at said at least one position through an illumination light beam having a predetermined illuminating pattern, wherein the illumination light beam creates an illuminated pattern covering partially a cornea of the eye and partially an iris of the eye, capturing an image of the iridocorneal zone at said at least one position including the illuminated pattern, measuring pattern deformation between the illuminating pattern and the illuminated pattern, and computing the amplitude of an iridocorneal angle based on the pattern deformation.

A third aspect of the present invention corresponds to a method of evaluating an iridocorneal angle at at least one position of an iridocorneal zone of an eye, comprising the steps of: illuminating the iridocorneal zone at said at least one position through an illumination light beam having a predetermined transversal cross-sectional shape, wherein the illumination light beam creates an illuminated pattern covering partially a cornea of the eye and partially an iris of the eye, capturing an image of the iridocorneal zone at said at least one position including the illuminated pattern, and processing the captured image of the iridocorneal zone based on the illuminating pattern and illuminated pattern.

Both these methods are suitable for being carried out in a very effective way through the optical equipment set out above even if not necessarily.

It is to be understood that, according to the present invention, the observation of the iridocorneal zone of the eye is obtained only thanks to artificial illumination light that is first back-scattered by tissues in the iridocorneal zone and is then detected, i.e. consists of (two-dimensional visual) images, according to its ordinary meaning. Therefore, the present technique should not be confused with e.g. OCT [Optical Coherence Tomography] that is a three-dimensional imaging technique based on interferometry—see for example document WO2013188885A1.

BRIEF DESCRIPTION OF DRAWINGS

The accompanying drawings, which are incorporated herein and constitute a part of the specification, illustrate exemplary embodiments of the present invention and, together with the detailed description, explain these embodiments. In the drawings:

FIG. 1 shows a simplified cross-section view (FIG. 1A) and a simplified front view (FIG. 1B) of an eye, FIG. 9 shows a second possible (Cartesian) visualization of an examination carried out through an equipment according to the present invention, and FIG. 10 show very schematically (A) an example of an illuminating pattern, (B) an example of an illuminated pattern in case of a normal-condition iridocorneal angle, (C) an example of an illuminated pattern in case of an iridocorneal angle more open than normal-condition, (D) an example of an illuminated pattern in case of an iridocorneal angle more close than normal-condition.

DETAILED DESCRIPTION

The following detailed description of exemplary embodiments refers to the accompanying drawings.

The following detailed description does not limit the present invention. Instead, the scope of the present invention is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1A:
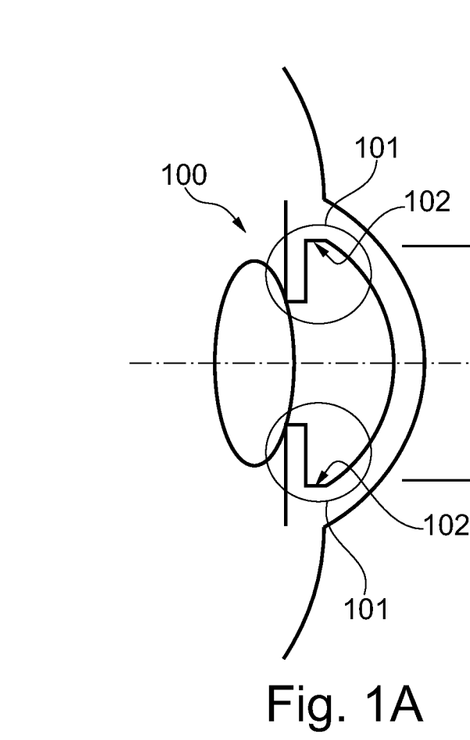

In FIG. 1, the eye is labeled 100 and its iridocorneal annular zone 101; considering FIG. 1A, as known, the iridocorneal annular zone 101 is substantially delimited on the left side by the iris, on the right side by an annular portion of the cornea, and on the intermediate side by the trabecular meshwork and adjacent tissues 102.

The optical equipment according to the present invention is designed for observation of at least a portion of an iridocorneal annular zone of an eye. Preferred embodiments of such equipment allow observation of the whole annular zone, i.e. the annular portion has an amplitude of 360° as in FIG. 1B. Alternative embodiments of such equipment may allow observation for example of portions having amplitude of 180° or 120° or 90°.

The status of the trabecular meshwork and the adjacent tissues in the iridocorneal zone are of particular importance for the diagnosis of glaucoma.

Figure 1B:
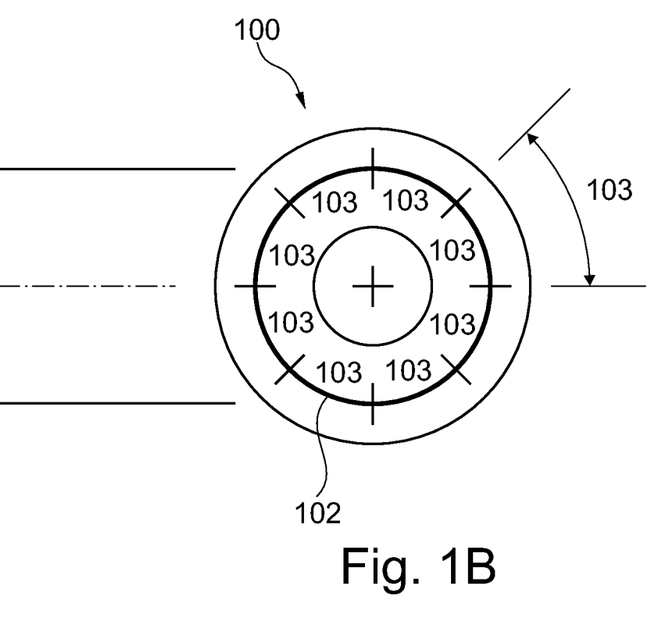

The 360° portion of the iridocorneal zone of FIG. 1B is divided in a number of sub-portions 103; in particular, by way of example, it is divided in eight sub-portions 103 having the same amplitude of 45°. It is to be noted that according to alternative embodiments, the number of sub-portions may be different; for example, may be six or seven or eight or nine or ten or eleven or twelve or thirteen or fourteen or fifteen or sixteen or seventeen or nineteen or twenty or twenty-one or twenty-two or twenty-three or twenty-four or even a higher number up to e.g. thirty-six.

In the following, for the sake of simplicity, it is assumed that an illumination optical path of an illumination light beam ends at the center of one sub-portion, that the illumination light beam illuminates at least one whole sub-portion, that an imaging optical path of an imaging light beam starts from the center of one sub-portion, that the imaging light beam carries image information of one whole sub-portion.

FIG. 2, FIG. 3, FIG. 4 and FIG. 5 relate to four alternative embodiments of the optical equipment according to the present invention. The first embodiment, i.e. the one shown in FIG. 2, will be described extensively; while the other three embodiments will be described more concisely due to the similarities with the first one. The same label 100 is used for the eye both in FIG. 1 as well as in FIG. 2, FIG. 3, FIG. 4, FIG. 5 due to the similarity of the figures and to the common assumption that the iridocorneal annular zone is divided in eight sub-portions; anyway, as already said, the number of sub-portions according to the present inventions may be different.

According to the present invention, natural light that is rather diffused (i.e. coming from different directions) and rather weak does not allow the desired observation of the iridocorneal annular zone of an eye; all gonioscopic lenses, including the one disclosed in document EP1464271A1, use natural light.

According to the present invention, the (artificial) light beams illuminating the iridocorneal zone of the eye enter the eye at a high inclination with respect to the eye axis, preferably higher than 45°.

Figure 2:
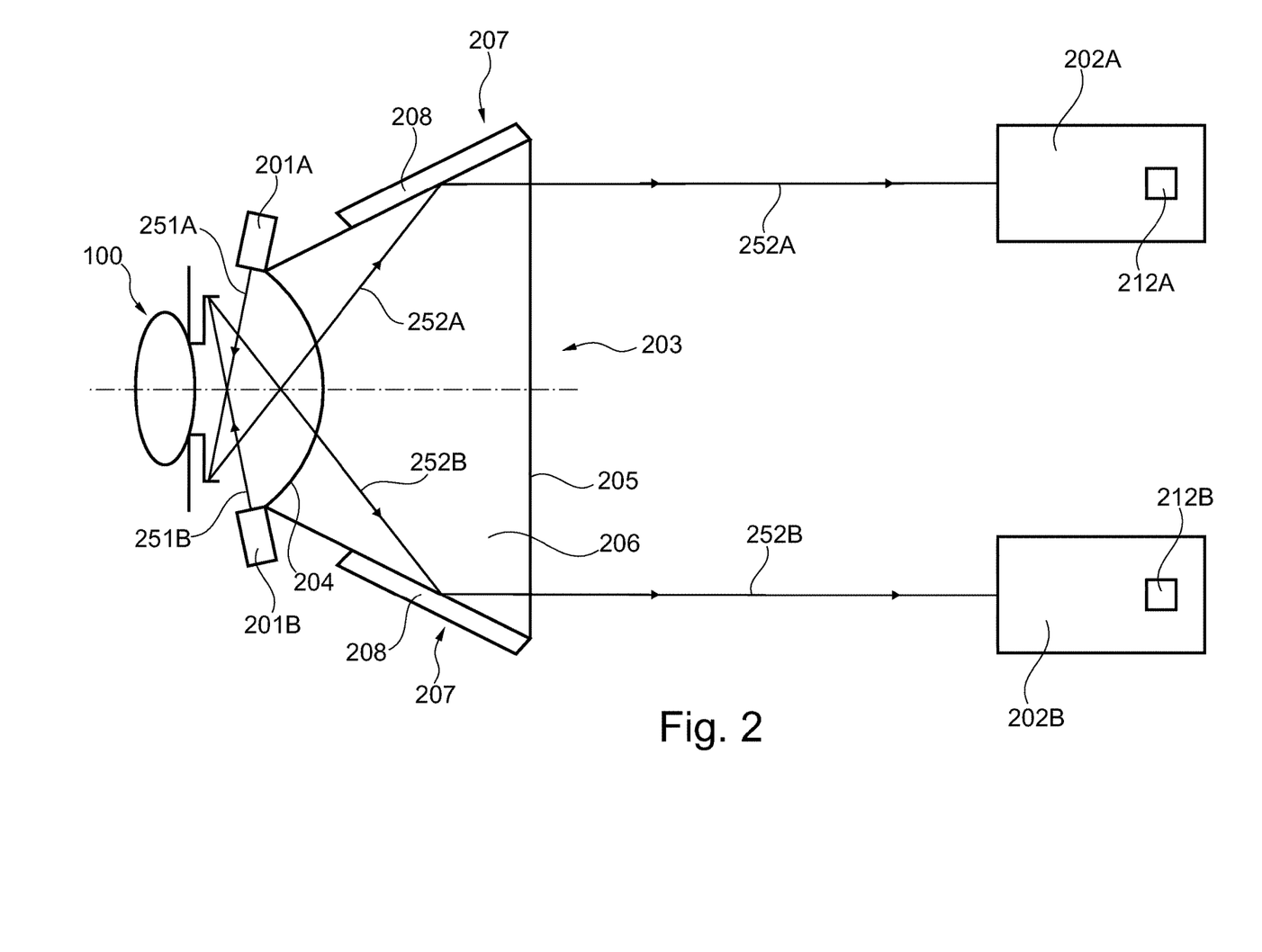
FIG. 2 shows a simplified block diagram of a first embodiment of the optical equipment according to the present invention.
Figure 3A:
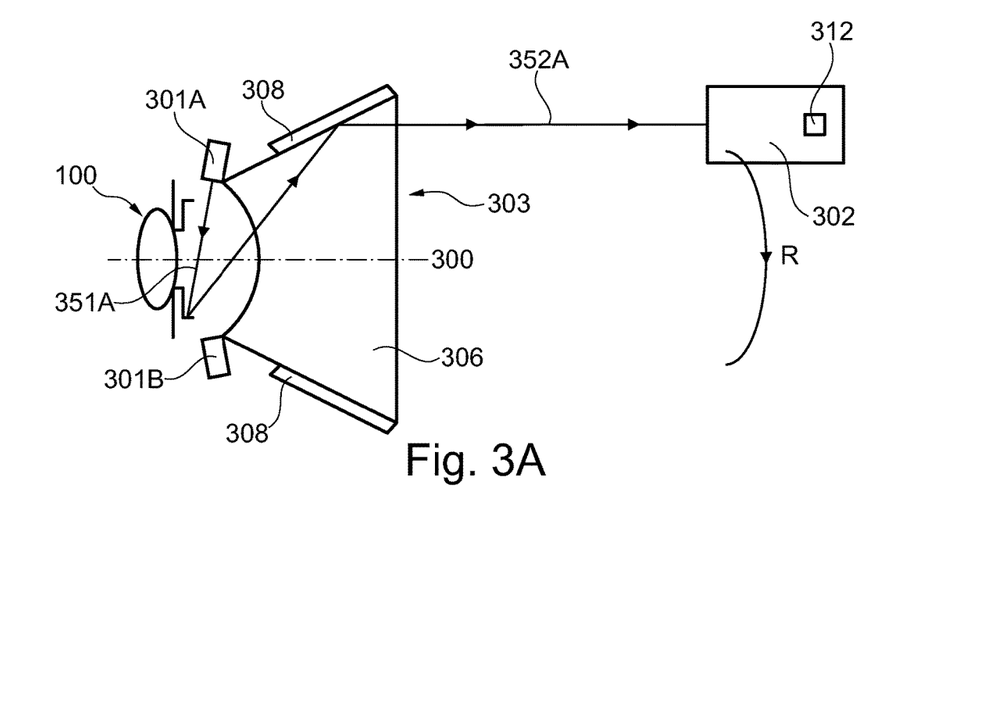
FIG. 3 shows a simplified block diagram of a second embodiment of the optical equipment according to the present invention in two different operating conditions A and B.
Figure 3B:
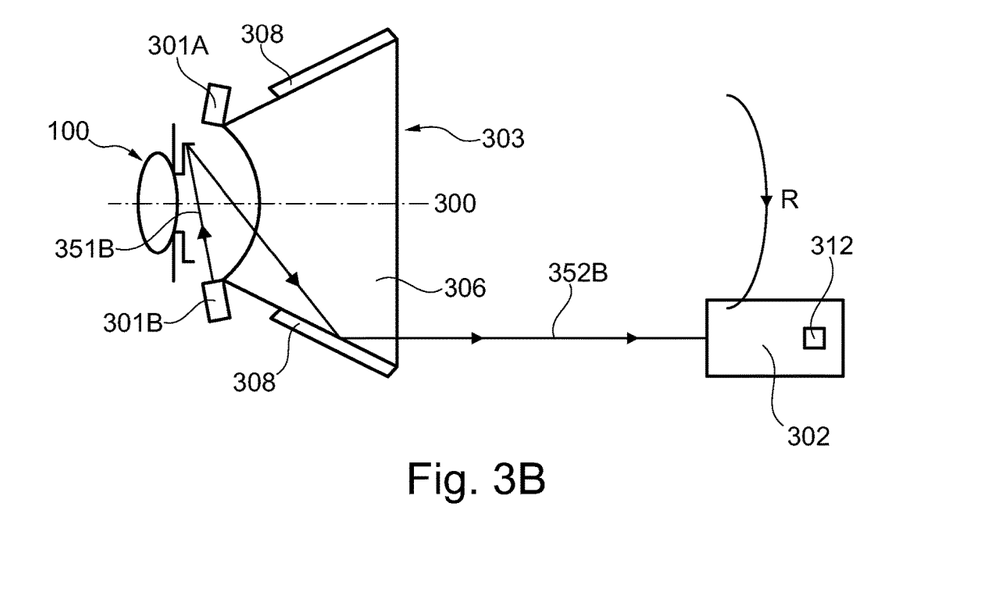

The equipment of FIG. 2 is suitable for observation of the whole iridocorneal annular zone of an eye and comprises: an illumination assembly consisting of e.g. eight illumination electric (in particular electronic) devices (only a first device 201A and a second device 201B are shown in FIG. 2), an image capturing assembly consisting of e.g. eight image capturing electric (in particular electronic) devices (only a first device 202A and a second device 202B are shown in FIG. 2), and a front optical assembly 203; each image capturing device 202 has a light sensor 212 consisting of a matrix of e.g. 256×256 light detectors.

All the illumination devices 201 and all the image capturing devices 202 operate at the same time; therefore, panoramic (rectangular or annular) picture of the whole iridocorneal annular zone of an eye may be obtained in a very short time by "stitching", i.e. combining electronically, the eight images of the image capturing devices (along a line or a circle).

In FIG. 2, the light sensors 212 of the image capturing devices 202 are shown as separate sensors; anyway, alternatively, they may be portions of a large light sensor consisting of a matrix of e.g. 4096×4096 light detectors.

Each of the illumination devices is associated to a distinct and different illumination optical path that goes to a corresponding sub-portion (see e.g. elements 103 in FIG. 1) of the iridocorneal annular zone of an eye; for example, device 201A is associated to path 251A and device 201B is associated to path 251B.

Each of the image capturing devices is associated to a distinct and different imaging optical path that comes from a corresponding sub-portion (see e.g. elements 103 in FIG. 1) of the iridocorneal annular zone of an eye; for example, device 202A is associated to path 252A and device 202B is associated to path 252B.

The front optical assembly 203 has a front surface 204 designed to be located close, i.e. at a short distance, to the front surface of an eye 100, a rear surface 205 designed to be located far, i.e. at a long distance, from the front surface of an eye 100; a viscous optical coupling agent, for example an ophthalmic gel, is applied on the front surface of the optical assembly and/or to the outside surface of the cornea before applying the optical assembly to the eye. According to a good practice, the above-mentioned "short distance" between the front surface of the assembly and the front surface of the eye should be the range 0.5-2.5 mm, preferably in the range 1.0-2.0 mm; shorter distances and longer distances have preferably to be avoided; in particular contact between the assembly and the eye has preferably to be avoided. The above-mentioned "long distance" depends on the length of front optical assembly and is preferably in the range 1-4 cm, more preferably in the range 1.5-2.5 cm.

The assembly 203 comprises a central portion 206 located between the front surface 204 and the rear surface 205 and a lateral portion 207 located around the central portion 206 and surrounding completely (i.e. it is 360° wide). According to this embodiment, the central portion 206 is a solid transparent prism having the shape of truncated octagonal pyramid; the front surface 204 is concave (corresponding to the convex outside surface of the cornea); according to this embodiment, the lateral portion 207 consists of a single-piece reflecting element 208 adjacent to the lateral surface of prism so that it has eight reflecting surfaces facing the central portion 206; it is to be noted that, according to this embodiment and by way of example, element 208 does not cover the lateral surface of prism entirely; according to alternative embodiments, the reflecting element covers the lateral surface of prism entirely.

The assembly 203 and all its components (in the embodiment of FIG. 2, the central portion 206 and the lateral portion 207) is stationary; this means that a panoramic image of a whole iridocorneal annular zone of an eye may be obtained without moving it.

All the imaging optical paths, see e.g. paths 252A and 252B, pass through the central portion 206 between the front surface 204 and the rear surface 205; the reflecting element 208 is designed to provide a reflection along all the imaging optical paths.

Therefore, in use, at least the image capturing assembly, i.e. in this embodiment the image capturing devices 202, is far from the observed eye 100, preferably at a distance greater than 2.5 cm, more preferably greater than 4.0 cm.

It is to be noted that number of optical paths corresponds to the number of sub-portions of the iridocorneal annular zone.

The embodiment of FIG. 3 is similar to the embodiment of FIG. 2: the illumination electric (in particular electronic) devices 301 are identical to the illumination devices 201, and the front optical assembly 303 with its central portion 306 and its lateral portion (including the reflecting element 308) is identical to the front optical assembly 203 with its central portion 206 and its lateral portion 207 (including the reflecting element 208).

Differently, the embodiment of FIG. 3 comprises only one image capturing electric (in particular electronic) device 302 (with one light sensor 312) that is identical to e.g. the image capturing device 202A; anyway, differently from device 202A, device 302 is designed to have a rotational motion R about the axis 300 of the front optical assembly 303.

In a first operating condition (FIG. 3A), the illumination device 301A is active, generates an illumination light beam associated to an illumination optical path 351A (identical to path 251A); illumination light beam 351A is back scattered from a first sub-portion of the iridocorneal annular zone of the eye 100 and creates an imaging light beam associated to an imaging optical path 352A (identical to path 252A); this imaging light beam reach the sensor 312 and creates an image on it.

In a second operating condition (FIG. 3B) when the image capturing devices 302 is rotated by 180°, the illumination device 301B is active, generates an illumination light beam associated to an illumination optical path 351B (identical to path 251B); illumination light beam 351B is back scattered from a second sub-portion of the iridocorneal annular zone of the eye 100 and creates an imaging light beam associated to an imaging optical path 352B (identical to path 252B); this imaging light beam reach the sensor 312 and creates an image on it.

According to the embodiment of FIG. 3, the image capturing devices 302 is rotated step-by-step by e.g. 45° and correspondingly e.g. eight images are successively created on the sensor 312; these images are successively transferred from the sensor 312 to an electronic processing unit internal or external to the optical equipment.

It is to be noted that all the illumination devices 301 may be maintained active during the whole observation process.

Figure 4:
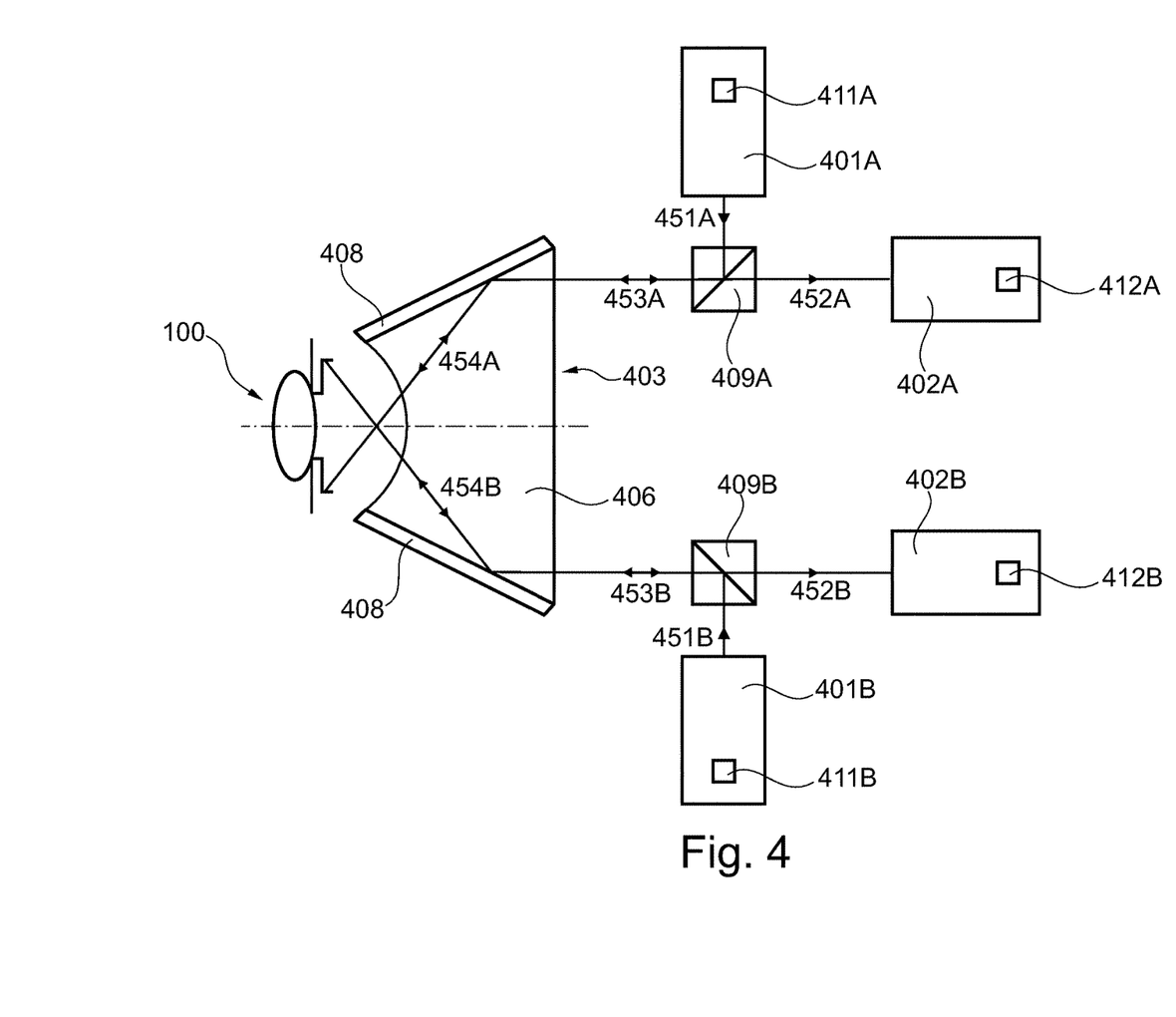
FIG. 4 shows a simplified block diagram of a third embodiment of the optical equipment according to the present invention.

The embodiment of FIG. 4 is similar to the embodiment of FIG. 2: the image capturing devices 402 (with one light sensor 412) are very similar to the image capturing devices 202, and the front optical assembly 403 with its central portion 406 and its lateral portion (including the reflecting element 408) is very similar to the front optical assembly 203 with its central portion 206 and its lateral portion 207 (including the reflecting element 208). It is to be noted that, according to this embodiment and by way of example, along the imaging optical paths 452 there are eight beam splitters 409 and that the element 408 covers the lateral surface of prism entirely; according to alternative embodiments, the reflecting element does not cover the lateral surface of prism entirely.

Differently, in the embodiment of FIG. 4, the illumination assembly comprises eight illumination electric (in particular electronic) devices 401 (each with one light emitter 411) that are far from the observed eye 100, preferably at a distance greater than 2.5 cm, more preferably greater than 4.0 cm. The eight illumination devices 401 generates eight illumination light beams associated to eight illumination optical paths 451; along all the paths 451 there is a first reflection provided by the beam splitters 409 and a second reflection provided by the element 408; all the paths 451 pass through the central portion 406 between the front surface and the rear surface of the front optical assembly 403. The imaging light beams starts from the sub-portions of the iridocorneal annular zone of an eye 100 and ends on the light sensors 412; all their imaging optical paths 452 pass through the central portion 406 between the front surface and the rear surface of the front optical assembly 403 and through the beam splitters 409; along all the paths 452 there is a reflection provided by the element 408. Therefore, paths 451 and 452 coincide in the way 453 between the beam splitters 409 and the element 408 and in the way 454 between the element 408 and the eye 100.

Figure 5:
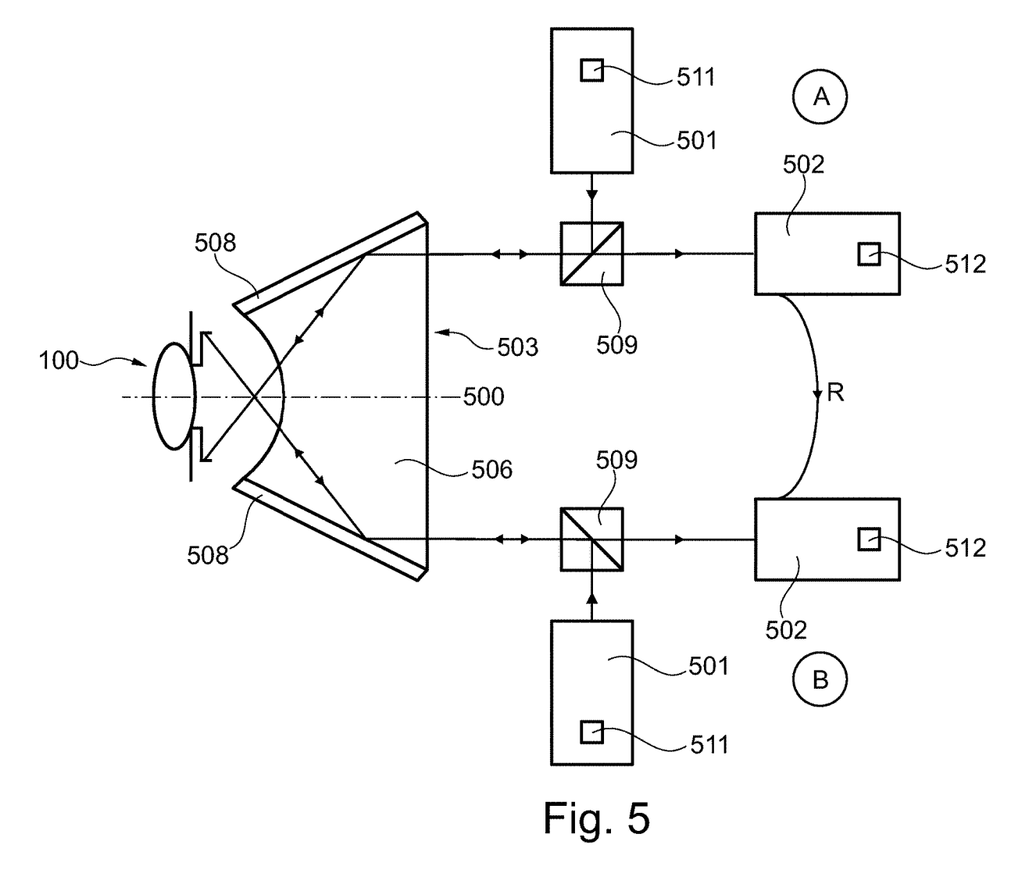
FIG. 5 shows a simplified block diagram of a fourth embodiment of the optical equipment according to the present invention—two different operating conditions A and B are shown in the same figure.

The embodiment of FIG. 5 is similar to the embodiment of FIG. 4 from the illumination and imaging optical paths point of view; furthermore, the front optical assembly 503 with its central portion 506 and its lateral portion (including the reflecting element 508) is identical to the front optical assembly 403 with its central portion 406 and its lateral portion (including the reflecting element 408).

Differently, the embodiment of FIG. 5 comprises only one illumination electric (in particular electronic) device 501 (with one light emitter 511), only one image capturing electric (in particular electronic) device 502 (with one light sensor 512) and only one beam splitter 509.

The illumination device 501 is identical to e.g. the illumination device 401A, the image capturing devices 502 is identical to e.g. the image capturing devices 402A, and the beam splitter 509 is identical to e.g. the beam splitter 409A. The illumination device 501, the image capturing devices 502, and the beam splitter 509 constitute one illumination-imaging assembly designed to have a rotational motion R about the axis 500 of the front optical assembly 503.

The first operating condition is shown on top of FIG. 5 and labeled A; it allows to illuminate and capture an image of a first sub-portion of the iridocorneal annular zone of the eye 100.

The second operating condition is shown on bottom of FIG. 5 and labeled B; it allows to illuminate and capture an image of a second sub-portion of the iridocorneal annular zone of the eye 100.

According to the embodiment of FIG. 5, the illumination-imaging assembly is rotated step-by-step by e.g. 45° and correspondingly e.g. eight images are successively created on the sensor 512; these images are successively transferred from the sensor 512 to an electronic processing unit internal or external to the optical equipment.

Figure 6:
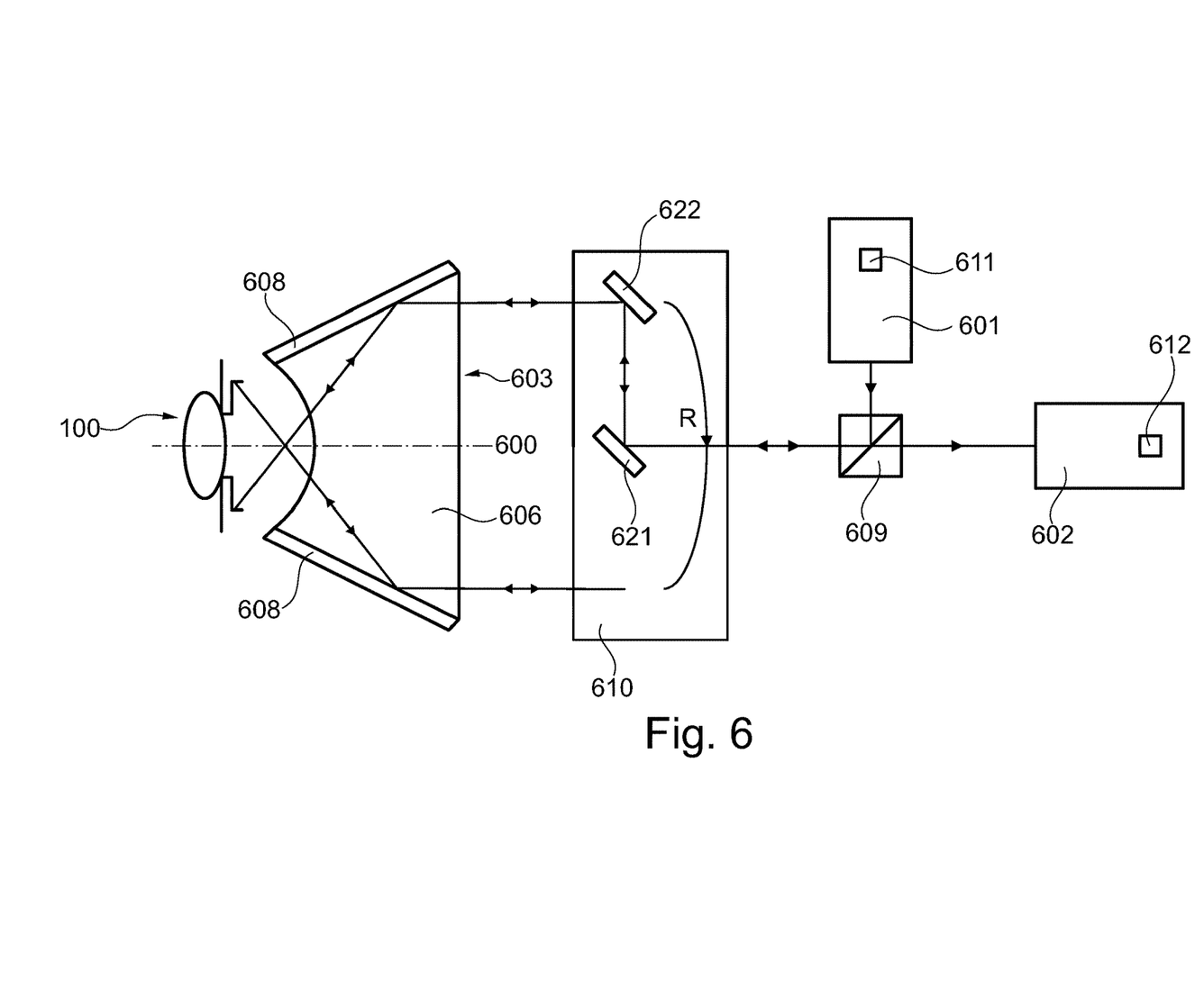
FIG. 6 shows a simplified block diagram of a fifth embodiment of the optical equipment according to the present invention.

Through the use in the equipment of a component in addition to those shown in FIG. 2, FIG. 3, FIG. 4 and FIG. 5, it is possible to observe the whole iridocorneal annular zone of an eye through only one stationary front optical assembly and only one image capturing assembly (including a relatively small light sensor consisting for example of a matrix of 256×256 light detectors) as shown in the embodiment of FIG. 6.

The equipment of FIG. 6 comprises a rear optical assembly 610 in addition to one stationary illumination electric (in particular electronic) device 601 (with one light emitter 611), one stationary image capturing electric (in particular electronic) device 602 (with one light sensor 612), one stationary front optical assembly 603 with its central portion 606 and its lateral portion (including the reflecting element 608), and one stationary beam splitter 609.

According to this embodiment, the rear optical assembly 610 has two functions distinct from each other: rotating the illumination light beam coming from the illumination device 601 and going to the eye 100 and rotating the imaging light beam coming from the eye 100 and going to the image capturing device 602. Both these rotations are around the symmetry axis 600 of the front optical assembly 603.

The rear optical assembly is rotary in the sense that some of its components are arranged to rotate, in particular to carry out a rotation motion (R in FIG. 6) around the symmetry axis of the front optical assembly. According to this embodiment there is a central mirror 621 and a lateral mirror 622; both mirrors 621 and 622 rotate around the symmetry axis 600 of the front optical assembly 603 step-by-step by e.g. 45° and correspondingly e.g. eight images are successively created on the sensor 612; these images are successively transferred from the sensor 612 to an electronic processing unit internal or external to the optical equipment; properly, the illumination light beam and the imaging light beam are rotated around the symmetry axis 600 of the front optical assembly 603 in their way between the eye 100 and the central mirror 621 and, parallelly, between the reflecting element 608 and the lateral mirror 622.

According to the embodiments of FIG. 3 and FIG. 5 and FIG. 6, there is a step-by-step rotation of one ore more components of the equipment (in particular of the illumination assembly, the image capturing assembly, the rear optical assembly); in other words, the illumination optical paths and/or the imaging optical paths are in finite number (according to these embodiments the number is equal to eight).

Alternatively, the rotation of one ore more components of the equipment (in particular of the illumination assembly, the image capturing assembly, the rear optical assembly) is continuous; in other words, the illumination optical paths and/or the imaging optical paths are in infinite number.

In the case of continuous rotation, the image capturing assembly may be arranged to capture images repeatedly (typically periodically) like a video camera.

In the case of continuous rotation, the illumination assembly may be arranged to emit a continuous light beam or an (e.g. periodically) intermittent light beam.

In the case of continuous rotation, the reflecting element of the front optical assembly has a reflecting surface shaped preferably like a cylinder lateral surface or a cone lateral surface while in the case of step-by-step rotation, the reflecting element has a reflecting surface shaped preferably like a prism lateral surface or a pyramid lateral surface.

An optical equipment according to the present invention typically comprises an electronic processing unit (that is not shown in any of the figures); the unit is arranged to control the equipment. In particular, it is electrically connected to the image capturing assembly and its one or more light sensors and is adapted to process the captured images; image processing may be fully automatic or semiautomatic, i.e. through the interaction with an operator.

Figure 7:
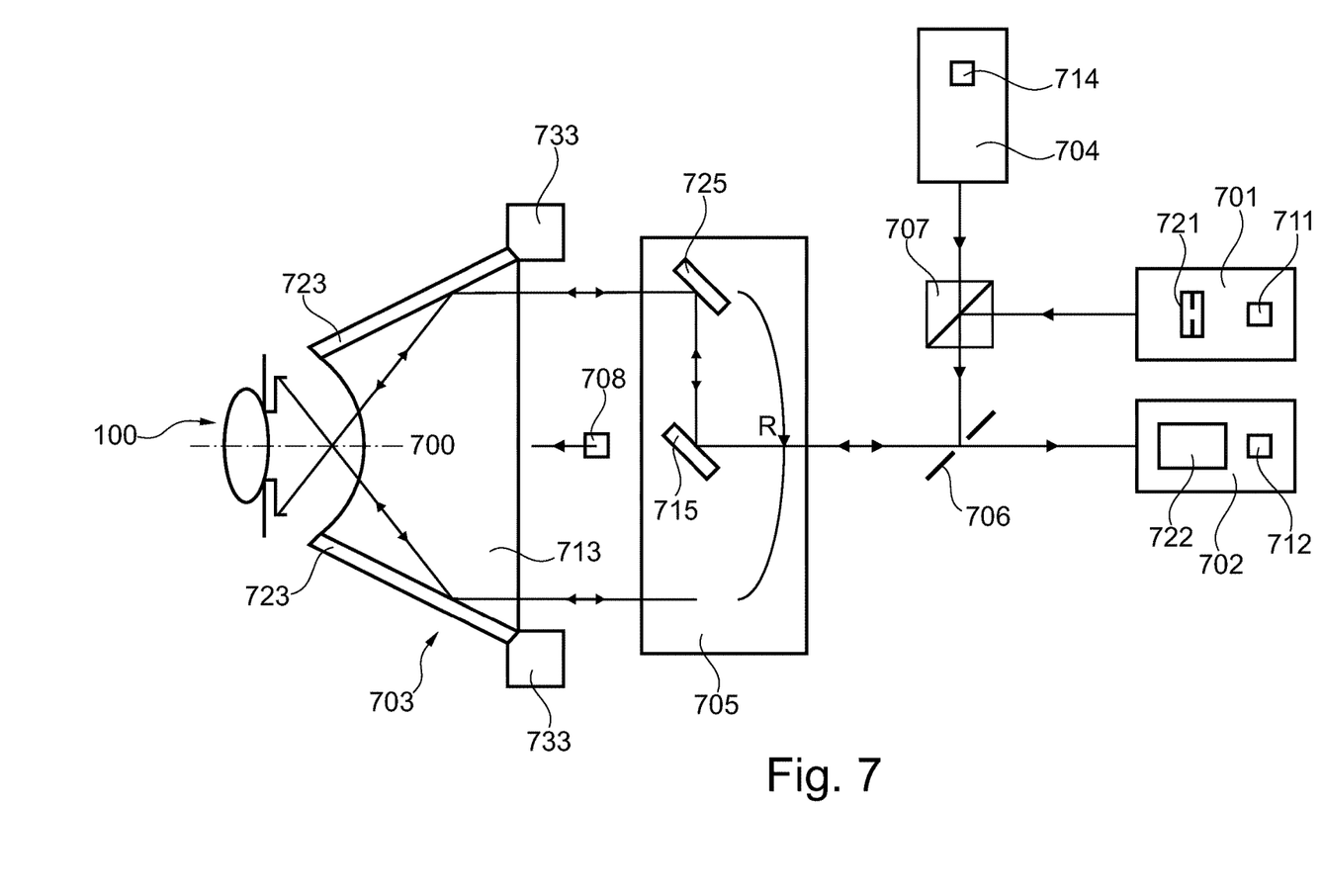
FIG. 7 shows a simplified block diagram of a sixth embodiment of the optical equipment according to the present invention.

FIG. 7 shows an embodiment of the optical equipment according to the present invention in a bit more detailed way that the other figures.

The embodiment of FIG. 7 is similar to the embodiment of FIG. 6 in that it comprises one stationary front optical assembly 703, one rotary rear optical assembly 705, one stationary image capturing electric (in particular electronic) device 702, and one stationary illumination assembly 701.

Additionally, it comprises one aiming assembly 704. Differently, it comprises and uses both one hollow mirror 706 and one beam splitter 707.

The components of the equipment of FIG. 7 are:

703: front optical assembly comprising a prism 713 with a reflecting element 723, and an annular frame 733; its optical axis is labeled 700;

705: rotary rear optical assembly with a rotary central mirror 715 and a rotary lateral mirror 725;

706: hollow mirror;

707: beam splitter;

702: image capturing assembly with a light sensor 712 and a light beam focusing system 722 (for example a movable focusing lens);

701: illumination with an illumination light beam emitter 711 and a light beam shaping system 721 (for example a slit);

704: aiming assembly with an aiming light beam emitter 714;

708: "fixation target", i.e. a light emitter for keeping the eye of the patient substantially fixed during examination in fact, due to the illumination light beam or beams might, the eye may be disturbed and turn.

In the embodiment of FIG. 7, the illumination assembly 701 is adapted to send an illumination light beam having a predetermined or selectable transversal cross-sectional shape so to create a predetermined or selectable illuminated pattern on a sub-portion of a portion of an iridocorneal annular zone of an eye; in general, the shape may derive from e.g. fixed or variable shaped apertures or fixed or variable diffractive optics; in this embodiment, there is one slit 721.

In the embodiment of FIG. 7, the image capturing assembly 702 is adapted to focus sub-portions of an iridocorneal annular zone of an eye at different focal planes; this is carried out through the focusing system 722.

In the embodiment of FIG. 7, the front optical assembly 703 is replaceable and is preferable provided with a bayonet mount integrated in the annular frame 733.

In the embodiment of FIG. 7, there is an aiming assembly 704 of a surgical laser system; the aiming assembly is adapted to send an aiming light beam, generated by emitter 714, toward the eye. In this case, both the front optical assembly 703 and the rear optical assembly 705 are adapted to transmit the aiming light beam.

In the embodiment of FIG. 7, there is a "fixation target" 708 coaxial with the axis 700 of the front optical assembly 703. It is to be noted that FIG. 7 is still a simplified block diagram of an equipment; therefore, other components may be present in a real equipment, for example one or more lenses or optical groups in one or more positions.

As already said, the images captured by an equipment according to the present invention may be processed by an electronic processing unit.

In general, according to the present invention, the iridocorneal angle at at least one position of an iridocorneal zone of an eye may be (not only observed but also) evaluated through the steps of:

illuminating the iridocorneal zone at said at least one position through an illumination light beam having a predetermined transversal cross-sectional (stationary) shape (see e.g. shape 1100 in FIG. 10), wherein the illumination light beam creates an illuminated (stationary) pattern (see e.g. shapes 1200, 1300 and 1400 in FIG. 10) covering partially a cornea (see e.g. area 1020 in FIG. 10) of the eye and partially an iris (see area 1030 in FIG. 10) of the eye, capturing an image of the iridocorneal zone at said at least one position including the illuminated pattern, and processing the captured image of the iridocorneal zone based on the illuminating pattern (see e.g. shape 1100 in FIG. 10) and illuminated pattern (see e.g. shapes 1200, 1300 and 1400 in FIG. 10).

In fact, for example by comparing the (external and/or internal) shape of illuminating pattern (e.g. 1100) and the (external and/or internal) shape of illuminated pattern (e.g. 1200, 1300 and 1400), it is possible to determine the morphology of the trabecular meshwork and/or the adjacent tissues.

Advantageously, such evaluation may be carried out all around the cornea as an equipment according to the present invention is typically able to capture an image (as a combination of a set of images) of the whole iridocorneal zone of an eye.

More specifically, according to the present invention, the amplitude of the iridocorneal angle at at least one position of an iridocorneal zone of an eye may be determined through the steps of:

illuminating the iridocorneal zone at said at least one position through an illumination light beam having a predetermined illuminating (stationary) pattern (see e.g. shape 1100 in FIG. 10), wherein the illumination light beam creates an illuminated (stationary) pattern (see e.g. shapes 1200, 1300 and 1400) covering partially a cornea (see e.g. area 1020 in FIG. 10) of the eye and partially an iris (see e.g. area 1030 in FIG. 10) of the eye, capturing an image of the iridocorneal zone at said at least one position including the illuminated pattern, measuring pattern deformation between the illuminating pattern (see e.g. shape 1100 in FIG. 10) and the illuminated pattern (see e.g. shapes 1200, 1300 and 1400), and computing the amplitude of an iridocorneal angle based on the pattern deformation.

In fact, the pattern deformation is related to the shape and size of the iridocorneal angle.

Advantageously, such determination may be carried out all around the cornea as an equipment according to the present invention is typically able to capture an image (as a combination of a set of images) of the whole iridocorneal zone of an eye.

Figure 10A:
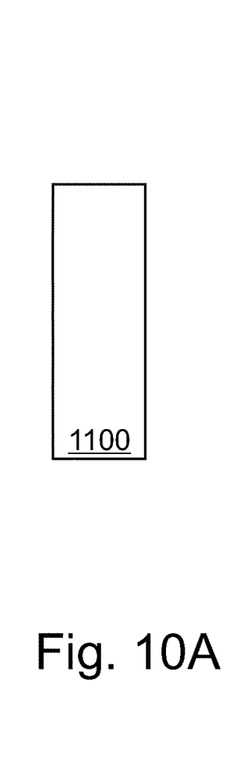
Figure 10B:
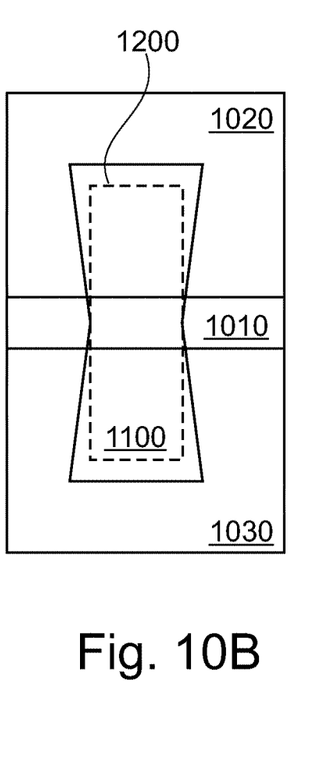
Figure 10C:
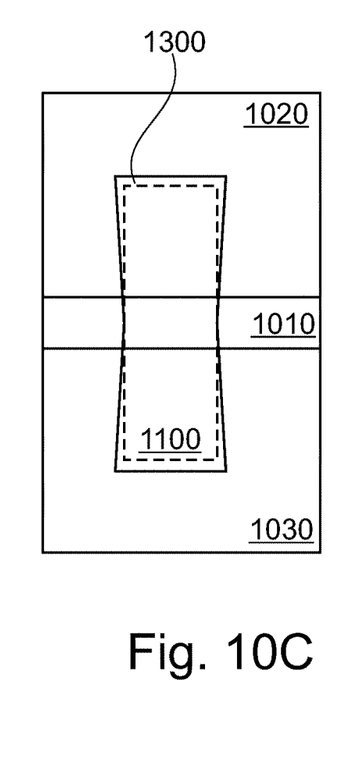
Figure 10D:
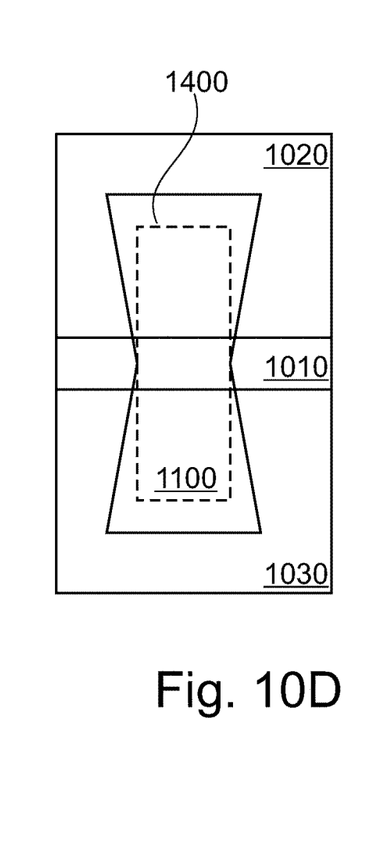

FIG. 10A shows an example of an illuminating pattern 1100; FIG. 10B shows an example of an illuminated pattern 1200 (as compared to the illuminating pattern 1100 in dashed line) in case of a normal-condition iridocorneal angle; FIG. 10C shows an example of an illuminated pattern 1300 (as compared to the illuminating pattern 1100 in dashed line) in case of an iridocorneal angle more open than normal-condition; FIG. 10D shows an example of an illuminated pattern 1400 (as compared to the illuminating pattern 1100 in dashed line) in case of an iridocorneal angle more close than normal-condition.

In FIGS. 10B, 10C and 10D, the illuminated patterns cover partially a cornea (area 1020 corresponds to a portion of the cornea as it may appears on an image captured by e.g. an optical equipment according to the present invention) of the eye and partially an iris (area 1030 corresponds to a portion of the iris as it may appears on an image captured by e.g. an optical equipment according to the present invention) of the eye, as well as a trabecular meshwork (area 1010 corresponds to a portion of the trabecular meshwork as it may appears on an image captured by e.g. an optical equipment according to the present invention) of the eye.

Considering FIGS. 10B, 10C and 10D, for example, it is apparent that each of the end portions of the illuminated patterns has shapes and sizes (for example its width and its length) that are different from the illuminating pattern and that are related to the amplitude of the iridocorneal angle: a small size corresponds to a narrow angle, a medium size corresponds to a normal angle, a big size corresponds to a wide angle. Such perceived deformations of the end portions of the illuminating pattern is due to the fact that, depending on the amplitude of the iridocorneal angle, the end portions are more or less focused (in FIGS. 10B, 10C and 10D, it is assumed that the trabecular meshwork is perfectly focused).

The electronic processing unit of an equipment according to the present invention may be arranged to carry out such evaluation, in particular such determination.

The electronic processing unit of an equipment according to the present invention is typically arranged to carried out also a visualization of the (whole) iridocorneal zone of an eye including the trabecular meshwork and the adjacent tissues.

Figure 8:
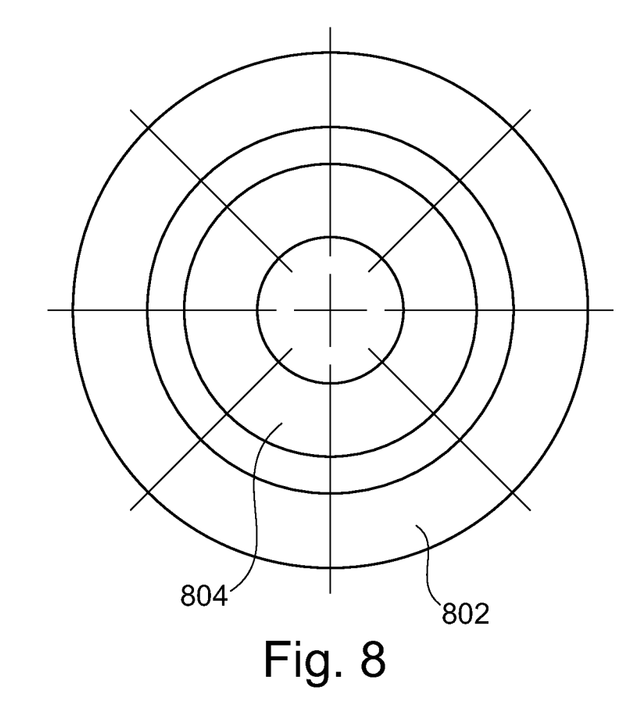
FIG. 8 shows a first possible (Polar) visualization of an examination carried out through an equipment according to the present invention.

FIG. 8 shows a first possible "Polar visualization" of an examination carried out through an equipment according to the present invention. For example, annular area 802 may contain a panoramic annular picture (for example obtained by "stitching" a plurality images along a circle) of the whole iridocorneal annular zone of an eye and annular area 804 may contain a Polar plot of the amplitude of the iridocorneal angle; typically, the annular picture and the Polar plot are aligned. Alternatively, the annular area 802 contains the plot and the annular area 804 contains the picture.

Figure 9:
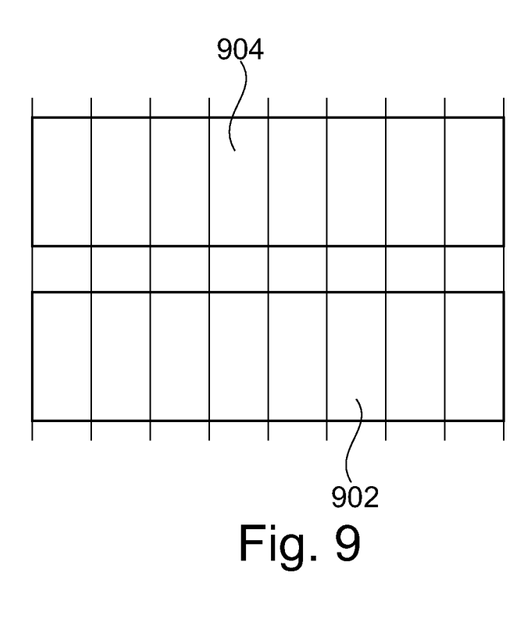

FIG. 9 shows a second possible "Cartesian visualization" of an examination carried out through an equipment according to the present invention. For example, rectangular area 902 may contain a panoramic linear picture (for example obtained by "stitching" a plurality images along a line) of the whole iridocorneal annular zone of an eye and rectangular area 904 may contain a Cartesian plot of the amplitude of the iridocorneal angle; typically, the linear picture and the Cartesian plot are aligned. Alternatively, the rectangular area 902 contains the plot and the rectangular area 904 contains the picture.

The invention claimed is:

1. Optical equipment suitable for observation of at least a portion of an iridocorneal annular zone of an eye comprising:
   an illumination assembly, comprising at least one illumination electric device, for illuminating at least a portion of an iridocorneal annular zone of an eye, and having a plurality of illumination optical paths for one or more illumination light beams going to a corresponding plurality of sub-portions of said portion,
   an image capturing assembly, comprising at least one image capturing electric device, for capturing images of at least a portion of an iridocorneal annular zone of an eye, and having a plurality of imaging optical paths for one or more imaging light beams coining from a corresponding plurality of sub-portions of said portion, and
   a front optical assembly having a front surface designed to be located close to the front surface of an eye, a rear surface designed to be located far from the front surface of an eye, and comprising a central portion located between the front surface and the rear surface and a lateral portion located around the central portion;
   wherein the front optical assembly is stationary;
   wherein all the imaging optical paths pass through the central portion between the front surface and the rear surface;
   wherein the lateral portion comprises a reflecting element surrounding the central portion and designed to provide a reflection along all the imaging optical paths;
   whereby, in use, at least the image capturing assembly is far from the observed eye;
   wherein the front surface of said front optical assembly is designed to be located at a distance of 0.5-2.5 mm from the front surface of the eye; and
   wherein the rear surface of said front optical assembly is designed to be located at a distance of 1-4 cm from the front surface of the eye.

2. Optical equipment according to claim 1,
   wherein, in use, the image capturing assembly is at a distance greater than 2.5 cm from the observed eye.

3. Optical equipment according to claim 1,
   wherein all the illumination optical paths pass through the central portion between the front surface and the rear surface, and
   wherein the reflecting element is designed to provide a reflection along all the illumination optical paths;
   whereby, in use, also the illumination assembly is far from the observed eye.

4. Optical equipment according to claim 3,
   wherein, in use, the illumination assembly is at a distance greater than 2.5 cm from the observed eye.

5. Optical equipment according to claim 1, wherein the reflecting element has a reflecting surface facing the central portion, wherein the reflecting surface is shaped like a cylinder lateral surface or a prism lateral surface or a cone lateral surface or a pyramid lateral surface.

6. Optical equipment according to claim 1, wherein the illumination optical paths and/or the imaging optical paths are in infinite number.

7. Optical equipment according to claim 1, wherein the illumination assembly comprises one or more light sources for sending one or more illumination light beams.

8. Optical equipment according to claim 7, comprising further a rear optical assembly, wherein the front optical assembly has a symmetry axis, and wherein the rear optical assembly is adapted to rotate the one or more illumination light beams around said symmetry axis.

9. Optical equipment according to claim 7, wherein the illumination assembly is adapted to send one or more illumination light beams having a predetermined or selectable transversal cross-sectional shape so to create a predetermined or selectable illuminated pattern on a sub-portion of a portion of an iridocorneal annular zone of an eye.

10. Optical equipment according to claim 1, wherein the image capturing assembly comprise one or more image detectors for receiving one or more imaging light beams coming from one or more sub-portions of a portion of an iridocorneal annular zone of an eye.

11. Optical equipment according to claim 10, comprising further a rear optical assembly, wherein the front optical assembly has a symmetry axis, and wherein the rear optical assembly is adapted to rotate the one or more imaging light beams around said symmetry axis.

12. Optical equipment according to claim 1, wherein the image capturing assembly is adapted to focus one or more sub-portions of a portion of an iridocorneal annular zone of an eye at different focal planes.

13. Optical equipment according to claim 1, comprising a light emitter for eye fixation.

14. Optical equipment according to claim 1, wherein the front optical assembly is replaceable.

15. Optical equipment according to claim 1, comprising a surgical laser system adapted to send an aiming light beam, wherein at least the front optical assembly is adapted to transmit the aiming light beam.

16. Optical equipment according to claim 1, comprising further an electronic processing unit electrically connected to said image capturing assembly and adapted to process images.

17. Optical equipment according to claim 16, wherein the electronic processing unit is adapted to generate a panoramic rectangular picture of the whole iridocorneal annular zone.

18. Optical equipment according to claim 16, wherein the electronic processing unit is adapted to generate a panoramic annular picture of the whole iridocorneal annular zone.

19. Method of determining an amplitude of an iridocorneal angle at at least one position of an iridocorneal zone of an eye, comprising the steps of:

illuminating the iridocorneal zone at said at least one position through an illumination light beam having a predetermined illuminating pattern, wherein the illumination light beam creates an illuminated pattern covering partially a cornea of the eye and partially an iris of the eye,     capturing an image of the iridocorneal zone at said at least one position including the illuminated pattern,     measuring pattern deformation between the illuminating pattern and the illuminated pattern, and     computing the amplitude of an iridocorneal angle based on the pattern deformation;

wherein a front surface of a front optical assembly, through which imaging optical paths pass, is designed to be located at a distance of 0.5-2.5 mm from the front surface of the eye;

wherein a rear surface of said front optical assembly is designed to be located at a distance of 1-4 cm from the front surface of the eye.

20. Method of evaluating an iridocorneal angle at at least one position of an iridocorneal zone of an eye, comprising the steps of:

illuminating the iridocorneal zone at said at least one position through an illumination light beam having a predetermined transversal cross-sectional shape, wherein the illumination light beam creates an illuminated pattern covering partially a cornea of the eye and partially an iris of the eye,     capturing an image of the iridocorneal zone at said at least one position including the illuminated pattern, and     processing the captured image of the iridocorneal zone based on the illuminating pattern and illuminated pattern;

wherein a front surface of a front optical assembly, through which imaging optical paths pass, is designed to be located at a distance of 0.5-2.5 mm from the front surface of the eye;

wherein a rear surface of said front optical assembly is designed to be located at a distance of 1-4 cm from the front surface of the eye.

\* \* \* \* \*